(12) United States Patent
Ditzel et al.

(10) Patent No.: US 8,450,521 B2
(45) Date of Patent: May 28, 2013

(54) CARBONYLATION PROCESS CATALYSED BY MORDENITE SUPPORTED ON INORGANIC OXIDES

(75) Inventors: Evert Jan Ditzel, East Yorkshire (GB); David John Law, Beverley (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 33 days.

(21) Appl. No.: 12/998,684

(22) PCT Filed: Oct. 8, 2009

(86) PCT No.: PCT/GB2009/002410
§ 371 (c)(1),
(2), (4) Date: May 18, 2011

(87) PCT Pub. No.: WO2010/058149
PCT Pub. Date: May 27, 2010

(65) Prior Publication Data
US 2011/0218356 A1  Sep. 8, 2011

(30) Foreign Application Priority Data
Nov. 19, 2008 (EP) .................................. 08253763

(51) Int. Cl.
*C07C 51/23* (2006.01)
*C07C 67/37* (2006.01)

(52) U.S. Cl.
CPC .................................... *C07C 67/37* (2013.01)
USPC .......................................... 560/232; 562/519

(58) Field of Classification Search
CPC ................................. C07C 67/37; C07C 69/24
See application file for complete search history.

(56) References Cited

U.S. PATENT DOCUMENTS
4,612,387 A  9/1986 Feitler
2006/0052236 A1* 3/2006 Angevine et al. ............... 502/66

FOREIGN PATENT DOCUMENTS
WO  WO 2006/121778  11/2006

OTHER PUBLICATIONS

International Search Report for PCT/GB2009/002435, mailed Dec. 23, 2009.
Written Opinion of the International Searching Authority for PCT/GB2009/002435, mailed Dec. 23, 2009.
Nawrocki, J. et al., "Trace metal impurities in silica as a cause of strongly interacting silanols", Chromatographia, vol. 28, No. 3/4, (1989), pp. 143-144.
Ellis, B. et al., "Heterogeneous catalysts for the direct, halide-free carbonylation of methanol", 11th International Congress on Catalysis—40th Anniversary, (Jun. 30, 1996), pp. 771-779.

* cited by examiner

*Primary Examiner* — Paul A Zucker
(74) *Attorney, Agent, or Firm* — Nixon & Vanderhye

(57) ABSTRACT

Process for preparing methyl acetate and/or acetic acid by contacting a carbonylatable reactant selected from dimethyl ether and methanol with carbon monoxide in the presence of a catalyst. The catalyst is a H-mordenite bound with a mesoporous binder selected from silicas, aluminas, silica-aluminas, magnesium silicates and magnesium aluminum silicates.

15 Claims, No Drawings

CARBONYLATION PROCESS CATALYSED BY MORDENITE SUPPORTED ON INORGANIC OXIDES

This application is the U.S. national phase of International Application No. PCT/GB2009/002410, filed 8 Oct. 2009, which designated the U.S., and claims priority to EP Application No. 08253763.0, filed 19 Nov. 2008, the entire contents of each of which are hereby incorporated by reference.

This invention relates to bound mordenite zeolites and their use as catalysts in the carbonylation of a carbonylatable reactant such as dimethyl ether and methanol.

Mordenite belongs to the class of materials referred to as zeolites. The structures of a large number of zeolites, including mordenite are well known and are defined, for example, in *The Atlas of Zeolite Framework Types* (C. Baerlocher, W. M. Meier, D. H. Olson, $5^{th}$ ed. Elsevier, Amsterdam, 2001). The web-based version (http://www.iza-structure.org/databases/) is a compendium of topological and structural details about zeolites including mordenite.

Zeolites in general have been used to catalyse a variety of different chemical processes including hydrocarbon conversion processes and the carbonylation of alcohols and ethers with carbon monoxide to produce carboxylic acids and/or esters.

Mordenites bound with a binder material have been demonstrated to be suitable for use as catalysts in hydrocarbon conversion processes such as the transalkylation of aromatic hydrocarbons, as described in U.S. Pat. No. 6,486,372 and the hydrocracking of high boiling hydrocarbon feedstocks, as described in WO 97/13826.

U.S. Pat. No. 4,612,387 discloses a method for making monocarboxylic acids and esters comprising contacting carbon monoxide and a monohydric alcohol containing 1 to 4 carbon atoms in the presence of a crystalline aluminosilicate zeolite having a silica:alumina ratio of at least about 6 and a constraint index within the approximate range of 1 to 12 under a pressure of at least one atmosphere.

Mordenite has also been disclosed as a catalyst in gas phase carbonylation processes employing dimethyl ether as carbonylatable reactant. For example, there is described in WO 2006/121778 a process for the production of a lower alkyl ester of a lower aliphatic carboxylic acid by carbonylating under substantially anhydrous conditions a lower alkyl ether, such as dimethyl ether, with carbon monoxide in the presence of a mordenite or ferrierite catalyst. There is no disclosure in WO 2006/121778 of the use of a mordenite which is bound with a binder material.

Inorganic oxide binder materials, such as aluminas, silicas, silica-aluminas, titanias and zirconias are generally considered to be inert materials and therefore it would be expected that a volume of catalyst bound with a binder material would demonstrate reduced catalytic activity compared to the same volume of catalyst but having no binder material present. Surprisingly, it has now been found that a catalyst for the carbonylation of dimethyl ether or methanol containing a mordenite in the acid form composited with a mesoporous inorganic oxide which serves as a binder results in improved catalytic performance, principally in terms of catalytic activity and/or selectivity compared to the catalytic performance achieved using the mordenite without a binder material.

Accordingly, the present invention provides a process for the preparation of methyl acetate and/or acetic acid product which process comprises contacting a carbonylatable reactant selected from dimethyl ether and methanol with carbon monoxide in the presence of a catalyst, wherein the catalyst is a H-mordenite bound with a mesoporous binder selected from silicas, aluminas, silica-aluminas, magnesium silicates and magnesium aluminum silicates.

The present invention also provides for the use of a mesoporous binder to improve the catalytic performance of H-mordenite in the carbonylation of a carbonylatable reactant selected from dimethyl ether and methanol with carbon monoxide, in which carbonylation there is used as the catalyst, H-mordenite bound with said binder and wherein the binder is selected from silicas, aluminas, silica-aluminas, magnesium silicates and magnesium aluminum silicates.

The catalyst for use in the present invention comprises a H-mordenite zeolite bound with a mesoporous binder selected from silicas, aluminas, silica-aluminas, magnesium silicates and magnesium aluminum silicates.

H-mordenite (also known as the acid form or hydrogen form of mordenite) is commercially available. Other forms of mordenite such as the sodium form or ammonium form are also available commercially. The sodium and ammonium forms of mordenite can be converted to H-mordenite by well-known techniques. For example, the ammonium form can be converted to the H-form by calcining the ammonium form at high temperature. The sodium form can be converted to the H-form by converting first to the ammonium form by ion exchange with ammonium salts such as ammonium nitrate and then calcining the ammonium form at high temperature.

Typically, mordenite has a silica:alumina ratio in the range 10 to 100:1 and such mordenites are suitable for use in the present invention. Preferably, however, the silica:alumina ratio of a H-mordenite for use in the present invention is in the range 10 to 40:1, such as 15 to 30:1.

Preferably, the Brunauer-Emmett-Teller (BET) surface area of the H-mordenite is in the range 100 to 500 $m^2/g$ as measured by nitrogen absorption. The measurement of BET surface area is described by Charles N. Satterfield in Heterogeneous Catalysis in Practice, McGraw-Hill Book company, 1980 p. 100-106.

For use as a catalyst in the process of the present invention, a H-mordenite is bound with a mesoporous binder selected from silicas, aluminas, silica-aluminas, magnesium silicates and magnesium aluminum silicates. The bound H-mordenite may be achieved by combining a H-mordenite with a binder or, alternatively, mordenite in its ammonium form may be combined with a binder and a bound H-mordenite is achieved by calcining the combined ammonium mordenite/binder mixture.

The mesoporous binder for use in the present invention is selected from at least one of the group of silicas, aluminas, silica-aluminas, magnesium silicates and magnesium aluminium silicates. Aluminas or silica-aluminas are particularly useful. Examples of suitable aluminas include boehmite type alumina and gamma alumina. Where a silica-alumina is used, its silica content is preferably in the range 5 to 40 wt %, suitably in the range 5 to 10 wt %. Preferably, the silica-alumina is amorphous.

Preferably, the binder is a refractory inorganic oxide such that the inorganic oxide is stable at high temperature, and, in particular is stable at temperatures which may be employed in calcination of the catalyst, such as a temperature of at least 400° C., for example, a temperature in the range 400 to 550° C.

The binder for use in the present invention is mesoporous. For the purposes of this invention, a mesopore is a pore having a diameter in the range of 2 to 50 nanometers and the expression 'mesoporosity' means the sum of the total surface area of the mesopores and the external surface area of the binder as measured by nitrogen BET. Suitably, the mesoporosity of the binder is in the range 1 to 500 $m^2/g$.

Preferably, the binder has a low microporosity. For the purposes of the present invention a micropore is a pore having a diameter of less than 2 nanometers and the expression 'microporosity' means the total surface area of the micropores of the binder as measured by nitrogen BET. Suitably, the microporosity of the binder material is in the range 1 to 100 m$^2$/g, preferably, in the range 1 to 10 m$^2$/g.

The amount of binder which can be used in the catalyst may vary but the amount is suitably that which achieves a maximum carbonylation rate in the carbonylation reaction. Suitably, the binder is present in an amount in the range of 10% to 80% by weight of the catalyst, preferably, in the range of 20% to 60% by weight of the catalyst or in the range 20 to 65% by weight of catalyst. In particular, the binder is present in the catalyst, in an amount in the range 35 to 65% by weight of catalyst. Suitably, where the binder is an alumina, such as a boehmite alumina, the binder is present in the catalyst, in an amount in the range 35 to 65% by weight of catalyst.

It has been found that binders which contain low levels of metallic impurities such as iron and the metals of Group 1 and Group 2 of the Periodic Table of Elements, for example, sodium, potassium, calcium and magnesium are particularly useful in the present invention. Thus, preferably, the total amount of metallic impurities present in the binder is in the range greater than 0 to 10 wt % and, more preferably, in the range greater than 0 to 7 wt %.

In a preferred embodiment of the present invention, the binder is an alumina or a silica-alumina which has a mesoporosity in the range 50 to 500 m$^2$/g, a microporosity of less than 10 m$^2$/g and has Group 1, Group 2 and iron metals present in a total amount of 0 to 1 wt %, preferably, in a total amount of 0 to 0.2 wt %, and wherein the binder is present in the catalyst in an amount in the range 10 to 80% by weight of catalyst.

In general, the catalyst for use in the present invention can be prepared by forming an intimate mixture of the binder and the H-form or ammonium form of mordenite, by, for example, slurry mixing or dry mixing of the binder and mordenite components. After mixing, the bound mordenite may be calcined. In general, calcination is carried out at a temperature in the range 400 to 500° C. but higher temperatures may be employed such as temperatures up to 550° C. Prior to use, the calcined catalyst may be pressed, crushed and sieved to form aggregates.

One method for preparing the catalyst of the present invention consists of slurry mixing the mordenite with the binder. Slurry mixing may be performed by mixing a mordenite, binder and deionised water, for a period necessary to obtain a wet homogeneous paste or slurry. The slurry is then dried, for example, at a temperature in the range 80 to 120° C. for several hours to remove any excess water and all or substantially all of the physi-sorbed water. The drying may be carried out either at atmospheric pressure or under reduced pressure. Optionally, prior to drying of the wet paste or slurry, it may be shaped by pressing, extruding or granulating to produce pellets, extrudates or beads. The dried slurry or shaped form of the slurry may then be calcined at a temperature in the range 400 to 550° C. for a period of from about 1 to 10 hours to form the catalyst.

Alternatively, the catalyst may be formed by dry mixing of the mordenite and binder components. Dry mixing may be performed by intimately mixing mordenite powder with dry binder to form a bound mordenite. The dry mixing may be carried out by any suitable mechanism, such as by tumbling or rotation. The bound mordenite may then be calcined. Calcination may be carried out a temperature in the range 400 to 550° C. for a period of from about 1 to 10 hours to form the catalyst.

The catalyst is used in a process for the production of methyl acetate and/or acetic acid product by carbonylating a carbonylatable reactant selected from dimethyl ether and methanol with carbon monoxide.

Where the carbonylatable reactant is dimethyl ether, it may be substantially pure or may contain low levels of inert impurities. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. For use in the process of the present invention the dimethyl ether feed may comprise small amounts of methanol provided that the amount of methanol present in the feed is not so great as to inhibit the carbonylation of dimethyl ether to methyl acetate product. It has been found that 5 wt % or less, such as 1 wt % or less of methanol may be tolerated in the dimethyl ether feed.

Alternatively, dimethyl ether may be generated in-situ from any suitable source, such as dimethyl carbonate. For example, liquid dimethyl carbonate may be contacted with gamma-alumina to decompose the dimethyl carbonate to dimethyl ether and carbon dioxide.

Suitably, the concentration of dimethyl ether in the gaseous feed is in the range of 0.1 to 20 mol %, based on the total gaseous feed (including any recycles).

The carbon monoxide may be substantially pure carbon monoxide, for example, carbon monoxide typically provided by suppliers of industrial gases, or it may contain impurities that do not interfere with the conversion of the carbonylatable reactant to the carbonylation product, such as nitrogen, helium, argon, methane and/or carbon dioxide.

Optionally, the carbonylation process of the present invention may be conducted in the presence of hydrogen. Suitably, therefore, the carbon monoxide feed may also contain hydrogen. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide.

Suitably, the molar ratio of carbon monoxide:hydrogen may be in the range 1:3 to 15:1, such as 1:1 to 10:1.

Where hydrogen is present in the process, it may be present at a partial pressure of at least 0.1 barg, such as 1 to 30 barg.

The molar ratio of carbon monoxide to carbonylatable reactant is suitably in the range 1:1 to 99:1, such as 2:1 to 60:1.

Where the carbonylatable reactant is methanol, water will be generated in-situ by the dimerisation of the methanol to ethers or via esterification of the methanol with acetic acid product. If desired, water may be added to the methanol feed. The amount of water added may be such that the molar ratio of methanol:water is in the range 50:1 to 2:1. The water may be fed separately to or together with the methanol feed. The water may be fed either as a liquid or as a vapour.

The carbonylation of dimethyl ether to methyl acetate does not generate water in-situ. Water has been found to inhibit the carbonylation of dimethyl ether to form methyl acetate. Thus, water is kept as low as is feasible. Preferably, therefore the carbonylation of dimethyl ether is conducted as an anhydrous process. To accomplish this, the dimethyl ether, carbon monoxide and catalyst are preferably dried prior to use in the process. However, small amounts of water can be tolerated without adversely affecting the formation of methyl acetate.

Suitably, water may be present in the gaseous feed to the process in an amount of 2.5 wt % or less, such as 0.5 wt % or less based on total gaseous feed (including recycles).

The process of the present invention may suitably be carried out at a temperature in the range of 100° C. to 400° C., such as 150 to 350° C.

The process of the present invention may be carried out at a pressure in the range 1 to 100 barg, such as 10 to 100 barg.

The Gas Hourly Space Velocity (GHSV) is suitably in the range 500 to 40,000 $h^{-1}$, such as 2000 to 20,000 $h^{-1}$.

It is preferred that the catalyst is activated immediately before use by heating the catalyst at elevated temperature for at least one hour under flowing nitrogen, carbon monoxide, hydrogen or mixtures thereof.

Preferably, the process of the present invention is carried out substantially in the absence of halides, such as iodide. By the term 'substantially' is meant that the total halide, for example, iodide content of the reactant gases (carbonylatable reactant and carbon monoxide) and catalyst is less than 500 ppm, preferably less than 100 ppm.

The process of the present invention is suitably carried out by passing carbonylatable reactant vapour, carbon monoxide gas and, optionally hydrogen gas, through a fixed bed, fluidised bed or moving bed of the catalyst maintained at the desired temperature and pressure.

If desired, the carbonylatable reactant may be contacted with a bed of alumina, such as corundum, immediately before the bed of catalyst.

The products of the process of the present invention are methyl acetate and/or acetic acid. Where the carbonylatable reactant is methanol, the predominant carbonylation product will be acetic acid but small amounts of methyl acetate may also be produced, depending on the degree of conversion of methanol. Where the carbonylatable reactant is dimethyl ether, the primary product of the process is methyl acetate but small amounts of acetic acid may also be produced. The acetic acid and/or methyl acetate produced by the process of the present invention can be removed in the form of a vapour and thereafter condensed to a liquid.

In addition to acetic acid and methyl acetate, the product stream from the process of the present invention may also comprise, unconverted dimethyl ether and/or unconverted methanol.

Methyl acetate and/or acetic acid may be recovered from the product stream by conventional techniques such as distillation.

The methyl acetate may be sold as such or it may be forwarded to other chemical processes. For example, at least part of the methyl acetate product may be hydrolysed to acetic acid.

Alternatively, at least part of the entire product stream of the present process, and which comprises methyl acetate, may be passed to a hydrolysis stage from which acetic acid is subsequently separated therefrom.

Hydrolysis of methyl acetate may be carried out by known techniques such as reactive distillation in the presence of an acid catalyst.

Acetic acid which is recovered from the product stream of the present invention or which is subsequently produced by hydrolysis of methyl acetate can be purified using conventional purification techniques, such as distillation.

The process of the present invention may be operated as either a continuous or a batch process, preferably as a continuous process.

The invention is now illustrated with reference to the following Examples.

EXAMPLE 1

Catalyst Preparation

A series of catalysts comprising 80 wt % H-mordenite and 20 wt % binder based on the total weight of the catalyst were prepared by Catalyst Preparation Method 1 or Catalyst Preparation Method 2 as described below.

Details of the binders used, the type and sources of the binders are given in Table 1 below. Physical and chemical properties of the binders are given in Table 2.

Catalyst Preparation Method 1

8 g of an ammonium-mordenite with a silica to alumina ratio of 20 (CBV21A ex Zeolyst) was mixed with 2 g of a binder. Sufficient deionised water was added to make a thick slurry and the mixture stirred thoroughly. The slurry was dried in an oven at 110° C. for at least 20 hours before being calcined in an oven under a static atmosphere of air. Calcination was carried out by increasing the temperature from room temperature to 90° C. at a ramp rate of 3° C./min. and held at this temperature for 2 hours. The temperature was then increased to 110° C. at a ramp rate of about 0.6° C./min and held at this temperature for 2 hours. Finally, the temperature was increased to 500° C. at a ramp rate of about 3.3° C./min and held at this temperature for 3 hours before being allowed to cool to room temperature. Prior to use the calcined catalyst was compacted at 12 tonnes in a 33 mm die set using a Specac Press, and then crushed and sieved to a particle size fraction of 250 to 500 microns.

Catalyst Preparation Method 2

4 g of ammonium mordenite with a silica to alumina ratio of 20 (CBV21A ex Zeolyst) in powder form was mixed with 2 g of a binder in a 500 ml Buchi powder drying flask and rotated at 100 rpm at ambient temperature and pressure for 1 hour. The mixture was then calcined according to the procedure described in Catalyst Preparation Method 1 above. Prior to use the calcined catalyst was compacted at 12 tonnes in a 33 mm die set using a Specac Press, and then crushed and sieved to a particle size fraction of 250 to 500 microns.

TABLE 1

| Binder | Origin/Source | Type |
| --- | --- | --- |
| Acti-Gel 208 | Active Minerals International | magnesium alumina silicate |
| Pural SB | Sasol | boehmite alumina |
| M907015 | BASF | magnesium alumina silicate |
| Chinafill 100 | Amberge Kaolinwerke | aluminosilicate clay |
| Chinafill 200 | Amberge Kaolinwerke | aluminosilicate clay |
| Bentonite | Aldrich | silicate clay |
| Kaolin-Aldrich | Aldrich | aluminosilicate clay |
| Ludox | Aldrich | silica |
| Montmorillonite K10 | Aldrich | silicate clay |
| CATALOX HTFa-101 | Sasol | boehmite alumina |
| CATALOX HTa-101 | Sasol | boehmite alumina |
| Puralox TH100/150 | Sasol | boehmite alumina |
| Puralox SCFa-140 | Sasol | boehmite alumina |
| Siral40 | Sasol | silica-alumina |
| Siral20 | Sasol | silica-alumina |
| Siral10 | Sasol | silica-alumina |
| Siral 5 | Sasol | silica-alumina |
| Kaolin-Zeochem | Zeochem | aluminosilicate clay |
| Pansil 400 | Tolsa | magnesium silicate |

TABLE 2

| Binder | Mesoporosity (m²/g) | Microporosity (m²/g) | Total metal* impurities (wt %) |
|---|---|---|---|
| Actigel | 120 | 55 | 5.01 |
| M 97015 | 111 | 33 | 6.67 |
| Pural SB | 274 | <10 | 0.19 |
| Chinafill 200 | <10 | <10 | 2.94 |
| Puralox TH100/150 | 134 | <10 | 0.05 |
| Puralox SCFa-140 | 126 | <10 | 0.14 |
| Siral 5 | 332 | <10 | 0.14 |
| Siral 10 | 347 | <10 | 0.14 |
| Siral 20 | 376 | <10 | 0.05 |
| Siral 40 | 457 | <10 | 0.05 |
| Catalox HTFa-101 | 80 | <10 | 0.08 |
| Montmorillonite K-10 | 250 | <10 | 4.35 |
| Pansil 400 | 237 | <10 | 4.70 |
| Kaolin (Zeochem) | 10 | <10 | 2.01 |
| Chinafill 100 | <10 | <10 | 4.42 |
| Kaolin (Aldrich) | 17 | <10 | 0.86 |
| Bentonite | 42 | 24 | 7.09 |
| Ludox | 163 | <10 | 0.96 |

*metal impurities are Na, K, Ca, Mg and Fe. NB for those binders which are magnesium silicates or magnesium alumina silicates, magnesium is not considered to be a metallic impurity.

Carbonylation Reaction

Each of the H-mordenite catalysts prepared from each of the binders identified in Table 1 above were used to catalyse the carbonylation of dimethyl ether as follows. H-mordenite (calcined CBV21A, ex Zeolyst) in the absence of a binder was also tested. The carbonylation reactions were carried out on a pressure flow reactor unit comprising 16 reactors. A Hastelloy reactor tube fitted with an integral electrical heating jacket was packed with 0.6 ml of a catalyst and 0.2 g of a gamma alumina pre-bed. The reactor and heating jacket were installed on the unit in a heated cabinet. The temperature of the catalyst bed was controlled by the integral heating jacket and the temperature of the pre-bed was controlled by the heated cabinet. The reactor was heated at atmospheric pressure under a flow of nitrogen to 130° C. in the heated cabinet and maintained at this temperature. The feed gas was then changed to 80 mol % carbon monoxide and 20 mol % hydrogen and the system was pressurised to 20 barg. The gas flow rate (GHSV) for these and all subsequent steps was 5000 hr$^{-1}$. The reactor was heated to 300° C. at a ramp rate of 3° C. per minute and the reactor maintained at these conditions for two hours, after which time the carbonylation reaction was started by introducing a gaseous feed of 76 mole % carbon monoxide, 19 mole % hydrogen and 5 mole % dimethyl carbonate into the reactor. A constant flow of reaction off-gases was taken from the high pressure side of the reactor, let down to atmospheric pressure at a temperature of at least 130° C. and passed to a gas chromatograph for analysis of acetyls products (methyl acetate and acetic acid).

The results of the carbonylation reactions are given in Table 3 below. The space time yield (STY) to acetyls products was calculated as follows:

Acetyls STY=AcOH STY+60/74*MeOAc STY

Acetyls STY (g kg$_{cat}^{-1}$ h$^{-1}$) is the STY based on the total weight of H-mordenite and binder components Acetyls STY (g kg$_{MOR}^{-1}$ h$^{-1}$) is the STY based on the weight of H-mordenite in the combined H-mordenite and binder mixture.

TABLE 3

| Binder | Catalyst Preparation Method | Acetyls STY (g kg$_{cat}^{-1}$ h$^{-1}$) at 20 h | Acetyls STY (g kg$_{MOR}^{-1}$ h$^{-1}$) at 20 h |
|---|---|---|---|
| None (H-mordenite only) |  | 181 | 181 |
| Actigel | 1 | 206 | 258 |
| Pural SB | 1 | 346 (a) | 433 (a) |
| M 97015 | 1 | 206 | 257 |
| Chinafill 200 | 1 | 253 (b) | 317 (b) |
| Chinafill 100 | 1 | 186 | 232 |
| Pural SB | 2 | 357 | 446 |
| Chinafill 100 | 2 | 186 | 233 |
| Kaolin (Aldrich) | 2 | 210 | 262 |
| Kaolin (Zeochem) | 2 | 258 | 322 |
| Siral 5 | 2 | 412 | 515 |
| Siral 10 | 2 | 375 | 469 |
| Siral 20 | 2 | 292 | 365 |
| Siral 40 | 2 | 318 | 397 |
| Puralox TH100/150 | 2 | 338 | 422 |
| Puralox SCFa-140 | 2 | 342 | 427 |
| Catalox HTFa-101 | 2 | 367 | 459 |
| Montmorillonite K-10 | 2 | 317 | 396 |
| Pansil 400 | 2 | 370 | 463 |
| Bentonite | 2 | 277 | 346 |
| Ludox | 2 | 310 | 387 |

(a) This result is an average of two carbonylation runs
(b) This result is an average of three carbonylation runs In addition, a series of carbonylation reactions as described above were carried out, in which the carbonylation reaction was conducted in the presence of a binder with no H-mordenite present. No carbonylation activity was observed for any of the binders tested. The binders tested were Pural SB, Siral 5, Siral 10, Siral 40, Chinafill 200, Puralox SCFa-140, Kaolin, Montmorillonite K-10 and Pansil 400.

As can be seen from the results in Table 3 above, H-mordenite catalysts which contain binder have superior catalytic activity to a H-mordenite catalyst having no binder.

EXAMPLE 2

Catalyst Preparation

Catalyst A—H-mordenite
 10 g of ammonium mordenite of silica:alumina ratio of 20 (CBV21A, Zeolyst International) was calcined at 500° C. for 3 hours in static air to obtain H-mordenite.

Catalyst B—H-mordenite:Pural SCF (80:20)
 8 g of ammonium mordenite of silica:alumina ratio of 20 (CBV21A, Zeolyst International) and 2 g of Pural SCF binder (Sasol) were placed in a Büchi powder drying flask. The two powders were then blended on a rotor evaporator at 100 r.p.m. for 1 hour at ambient temperature and pressure. The blended ammonium mordenite/binder was then calcined for 3 hours at 500° C. under an atmosphere of static air to obtain the catalyst. Pural SCF is a boehmite alumina of mesoporosity 237 m2/g. microporosity of <10 m2/g and a total metal impurity level of 0.02 wt %.

Catalyst C—H-mordenite:Pural SCF (50:50)
 The preparation of catalyst B was repeated except that 10 g of ammonium mordenite of silica:alumina ratio of 20 (CBV21A Zeolyst International) and 10 g of Pural SCF (Sasol) were used.

Catalyst D—H-mordenite:Siral 5 (50:50)
 The preparation of catalyst B was repeated except that 10 g of ammonium mordenite of silica:alumina ratio of 20 (CBV21A, Zeolyst International) and 10 g of Siral 5 binder (Sasol) were used.

Catalyst E—H-mordenite:Siral 5 (20:80)

The preparation of catalyst B was repeated except that 2 g of ammonium mordenite of silica:alumina ratio of 20 (CBV21A, Zeolyst International) and 8 g of Siral 5 (Sasol) were used.

Carbonylation of Dimethyl Ether

Each of Catalysts A to E was used to catalyse the carbonylation of dimethyl ether with carbon monoxide in the presence of hydrogen using the apparatus and method described below. Prior to use 0.75 g of each catalyst was compacted at 10 tonnes in a 13 mm die set using a pneumatic press, and crushed and sieved to a particle size fraction of 125 to 160 microns.

The carbonylation reactions were carried out in a pressure flow reactor unit consisting of 16 identical reactors of the type described in WO 2005063372. Prior to the loading of a catalyst into the reactor, a 5 cm bed of steatite of sieve fraction of 100-350 μm was placed in the respective catalyst holder. A 5 cm zone of corundum of sieve fraction of 125-160 μm was placed on top of the steatite bed. On a dry mass basis (determined by loss on ignition of the relevant sample measured by heating the catalyst from room temperature to 600° C. at a ramp rate of 30° C. per minute) a 0.625 g sample of catalyst was then placed on top of the corundum bed. The catalyst was covered by a 5 cm corundum bed of a particle size of 125-160 μm. A 5 cm zone of steatite of sieve fraction of 100-350 μm was placed on top of the corundum bed. Every zone was concreted via hitting or vibrating to get a stable bed and a defined starting height of the catalyst zone. The catalyst was then pressurised to the a reaction pressure of 70 bar with a $CO/H_2$ at a molar ratio of 4:1 and a flow rate of 4 l/h. The catalyst was then heated at 0.5° C./min to a holding temperature of 220° C., where it was held for 3 hours and then ramped to 300° C. at 0.5 deg.C/min, followed by a dwell time of 3 hours. The gas feed was then changed to a mixture of carbon monoxide, hydrogen and dimethyl ether of molar ratio 72:18:10 at a flow rate of 4.275 l/h. Nitrogen gas was introduced at a variable rate of 0-50 ml/min to equalise the pressure swings between the 16 reactor exits. The exit stream from a reactor was passed to a gas chromatograph to determine the concentration of reactants and carbonylation products. The reaction was allowed to continue for 169 hours under conditions of 300° C., 70 bar, and a gas hourly space velocity (GHSV) of 4275 $h^{-1}$. From the gas chromatography analysis of the reactor effluent for methyl acetate (MeOAc) the space time yield (STY) of methyl acetate product was determined as grams of methyl acetate per kilogram of catalyst per hour. The carbonylation product was predominantly methyl acetate, with only small amounts of acetic acid being produced. The results of the carbonylation reactions are shown in Table 4 below.

Table 4 shows the results for catalysts A to E after 140 hours.

TABLE 4

| Catalyst | Binder | Binder/wt. % | MeOAc STY/ g $kg^{-1}$ of catalyst $h^{-1}$ (a) | MeOAc STY/ g $kg^{-1}$ of mordenite $h^{-1}$(b) |
|---|---|---|---|---|
| A | None | 0 | 199 | 199 |
| B | Pural SCF | 20 | 753 | 941 |
| C | Pural SCF | 50 | 780 | 1560 |
| D | Siral 5 | 50 | 640 | 1280 |
| E | Siral 5 | 80 | 284 | 1420 | a) STY expressed per kg of catalyst, including both the H-mordenite and binder components
b) STY expressed per kg of H-mordenite per hour, excluding the binder component Table 4 shows that the combination of H-mordenite with either Pural SCF or Siral 5 binder markedly improves the activity of H-mordenite compared to H-mordenite having no binder.

EXAMPLE 3

Catalyst F

Copper Mordenite 20 g of ammonium mordenite of silica:alumina ratio of 20 (CBV21A, Zeolyst International) and $Cu(NO_3)_2 \cdot 2.5H_2O$ (3.56 g) were added to deionised water (50 mL) and stirred for 12 hours at room temperature. The solution was concentrated in vacuo at 80° C. and then dried at 110° C. for 20 hours, before being calcined at 500° C. for 3 hours in an atmosphere of static air. The mordenite had a copper loading of approximately 55 mole % relative to Al contained in the mordenite.

Catalyst G

Copper Mordenite:Pural SCF (80:20)

15 g of ammonium mordenite of silica:alumina ratio of 20 (CBV21A, Zeolyst International) and $Cu(NO_3)_2 \cdot 2.5H_2O$ (2.67 g) were added to deionised water (40 mL) and stirred for 12 hours at room temperature. The solution was concentrated in vacuo at 80° C. and then dried at 110° C. for 20 hours. The mordenite had a copper loading of approximately 55 mole % relative to Al contained in the mordenite. 8 g of the dried copper mordenite was gently milled to obtain a free flowing powder and then added to a Büchi powder drying flask with 2 g of Pural SCF (Sasol) and rotated on a rotor evaporator with a speed of 100 r.p.m. for 1 hour at ambient temperature and pressure. The blended copper loaded mordenite/binder was then calcined at 500° C. for 3 hours under an atmosphere of static air.

Carbonylation of Dimethyl Ether

Each of catalysts F and G was used to catalyse the carbonylation of dimethyl ether using the carbonylation method described in Example 2 above. The results for catalysts F and G compared to catalysts A and B after 140 hours reaction time are given in Table 5 below.

TABLE 5

| Catalyst | Binder | Binder/ wt. % | Mordenite catalyst component | Acetyls STY/ g $kg^{-1}$ of catalyst $h^{-1}$ (a) | Acetyls STY/ g $kg^{-1}$ of mordenite $h^{-1}$ (b) | Selectivity to MeOAc/% (c) |
|---|---|---|---|---|---|---|
| A | None | 0 | H-mordenite | 164 | 164 | 93 |
| B | Pural SCF | 20 | H-mordenite | 610 | 763 | 95 |
| F | None | 0 | Cu-mordenite | 805 | 805 | 92 |
| G | Pural SCF | 20 | Cu-mordenite | 644 | 805 | 88 |

(a) STY expressed per kg of catalyst, including both the mordenite and binder components
(b) STY expressed per kg of mordenite component per hour, excluding the binder component
(c) Selectivity to methyl acetate based upon dimethyl ether converted From an inspection of Table 5, it can be seen that the combination of H-mordenite with binder (Catalyst B) markedly improves the activity of H-mordenite (Catalyst A) whereas the inclusion of binder in copper mordenite (Catalyst G) reduces the activity of the copper mordenite.

The high selectivity to methyl acetate is retained when H-mordenite (Catalyst A) is combined with binder (Catalyst B), whereas when copper mordenite (Catalyst F) is combined with binder (Catalyst G), the selectivity to methyl acetate decreases.

Furthermore comparing Catalyst B (bound H-mordenite) with Catalyst G (bound copper mordenite) shows that the two catalysts have similar activities but Catalyst B is significantly more selective to methyl acetate.

EXAMPLE 4

A number of experiments were conducted to determine the impact of the amount of binder on the catalytic performance of H-mordenite in carbonylation. A series of catalysts containing 10 to 80 wt % Pural SCF (ex Sasol) binder were prepared in accordance with the method for preparing Catalyst B (in Example 2 above) and sieved to a size in the range 125-160 microns. The performance of these catalysts and Catalyst A (H-mordenite as prepared in Example 2 above) was tested for the carbonylation of dimethyl ether. The carbonylation reactions were carried out as described in Example 1 above using 1.95 g of catalyst and a gaseous feed containing 6 mol % dimethyl ether, 0.5 mol % methyl acetate and carbon monoxide and hydrogen at a molar ratio of 4:1. The carbonylation reaction conditions were 300° C., 70 bar and a GHSV of 4000 h$^{-1}$. The results after 140 hours reaction time are given in Table 6 below.

TABLE 6

| Catalyst | Binder | Binder/ wt. % | MeOAc STY/ g kg$^{-1}$ of catalyst h$^{-1}$ (a) | MeOAc STY/ g kg$^{-1}$ of mordenite h$^{-1}$ (b) | Selectivity to MeOAc/ % (c) |
| --- | --- | --- | --- | --- | --- |
| A | None | 0 | 140 | 140 | 96.0 |
| H | Pural SCF | 10 | 279 | 310 | 97.2 |
| I | Pural SCF | 20 | 322 | 403 | 98.1 |
| J | Pural SCF | 35 | 446 | 686 | 98.6 |
| K | Pural SCF | 50 | 445 | 890 | 98.6 |
| L | Pural SCF | 65 | 437 | 1249 | 98.3 |
| M | Pural SCF | 80 | 232 | 1160 | 97.9 |

(a) STY expressed per kg of catalyst, including both the H-mordenite and binder components
(b) STY expressed per kg of H-mordenite per hour, excluding the binder component
(c) Selectivity to MeOAc based upon DME converted As can be seen from Table 6, as the amount of binder in the catalyst increases, the activity of the mordenite catalyst component also increases, to a maximum at approximately 65 wt % binder.

The invention claimed is:

1. A process for the preparation of methyl acetate and/or acetic acid product which process comprises contacting a carbonylatable reactant selected from dimethyl ether and methanol with carbon monoxide in the presence of a catalyst, wherein the catalyst is a H-mordenite bound with a mesoporous binder selected from silicas, aluminas, silica-aluminas, magnesium silicates and magnesium aluminum silicates.

2. A process according to claim 1 wherein the binder is selected from aluminas and silica-aluminas.

3. A process according to claim 2 wherein the alumina is a boehmite type alumina.

4. A process according to claim 2 wherein the silica-alumina has a silica content in the range 5 to 40 wt %.

5. A process according to claim 1 wherein the binder has a mesoporosity in the range 1 to 500 m$^2$/g as measured by nitrogen BET.

6. A process according to claim 1 wherein the binder has a microporosity in the range 1 to 100 m$^2$/g as measured by nitrogen BET.

7. A process according to claim 1 wherein the binder contains the metals of Group 1 and Group 2 of the Periodic Table of Elements and iron in a total amount in the range greater than 0 to 10 wt %.

8. A process according to claim 1 wherein the binder is present in the catalyst in an amount in the range 10 to 80% by weight of the catalyst.

9. A process according to claim 1 wherein the H-mordenite is bound with an alumina in an amount 35 to 65 wt % based on the total weight of H-mordenite and binder.

10. A process according to claim 1 wherein the H-mordenite is bound with an alumina or silica-alumina binder having a mesoporosity in the range 50 to 500 m$^2$/g, a microporosity of less than 10 m$^2$/g and 0 to 1 wt % in total of Group 1, Group 2 and iron metals and wherein the binder is present in the catalyst in an amount 10 to 80% by weight of catalyst.

11. A process according to claim 10 wherein the binder has 0 to 0.2 wt % in total of iron and the metals of Group 1 and Group 2 of the Periodic Table of Elements.

12. A process according to claim 1 wherein the carbonylatable reactant is dimethyl ether.

13. A process according to claim 12 wherein the process is carried out as an anhydrous process.

14. A process according to claim 1, in which process hydrogen is present.

15. A process according to claim 1 wherein the product of the process comprises methyl acetate and at least part of the methyl acetate product is hydrolysed to acetic acid.

* * * * *